(12) United States Patent
Erhardt et al.

(10) Patent No.: US 6,846,937 B2
(45) Date of Patent: Jan. 25, 2005

(54) METHOD FOR THE SELECTIVE REMOVAL OF ACYL-FUNCTIONALITY ATTACHED TO THE 2'-HYDROXY-GROUP OF PACLITAXEL-RELATED DERIVATIVES

(75) Inventors: Paul W. Erhardt, Sylvania, OH (US); Wieslaw A. Klis, Toledo, OH (US); Jeffery G. Sarver, Rossford, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 10/491,576
(22) PCT Filed: Sep. 27, 2002
(86) PCT No.: PCT/US02/30727
§ 371 (c)(1),
(2), (4) Date: Apr. 2, 2004
(87) PCT Pub. No.: WO03/030815
PCT Pub. Date: Apr. 17, 2003

(65) Prior Publication Data
US 2004/0181079 A1 Sep. 16, 2004

Related U.S. Application Data
(60) Provisional application No. 60/327,406, filed on Oct. 5, 2001.

(51) Int. Cl.⁷ ............................................. C07D 305/14
(52) U.S. Cl. ....................................... 549/510; 549/511
(58) Field of Search .................................. 549/510, 511

(56) References Cited

U.S. PATENT DOCUMENTS
5,679,807 A * 10/1997 Murray et al. ............... 549/510

* cited by examiner

Primary Examiner—Ba K. Trinh
(74) Attorney, Agent, or Firm—MacMillan, Sobanski & Todd, LLC

(57) ABSTRACT

A method for removing acyl-groups appended by an ester linkage to the 2'-hydroxyl group present in paclitaxel-related molecules comprising treatment with alcohol under non-acidic conditions. 2',7-bis-Monochloroacetylpaclitaxel analogs are converted to their corresponding 7-monochloroacetyl derivatives by treatment with alcohol under non-acidic conditions

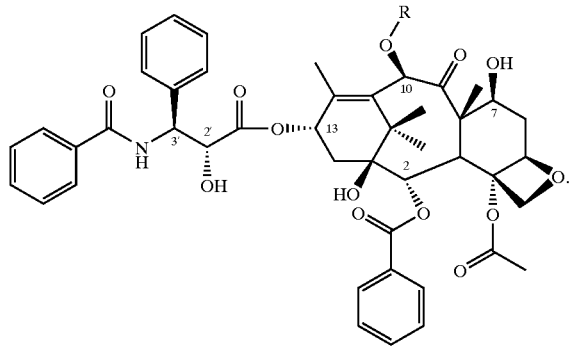

14 Claims, 5 Drawing Sheets

Figure 2 - Table 1

Stability of PAC and DAP CAC analogs in methanol (1 mg/ml) at ambient temperature.

| Compound | RT (min.) | NMR C2'H | $T_{1/2}$ (hours) | Product |
|---|---|---|---|---|
| 2',7,10-tri-CAC-DAP† | 17.7 | 5.58 | 5.6 | 7,10-bis-CAC-DAP |
| 2',7-bis-CAC-DAP† | 12.2 | 5.59 | 5.5 | 7-CAC-DAP |
| 2'-CAC-DAP | 6.0 | 5.55 | 18.1 | DAP |
| 2',7-bis-CAC-PAC† | 16.6 | 5.59 | 6.4 | 7-CAC-PAC |
| 2'-CAC-PAC†† | 8.3 | 5.55 | 4.3 | PAC |
| 7,10-bis-CAC-DAP | 14.2 | 4.80 | >>72* | --- |
| 7-CAC-DAP | 8.2 | 4.78 | >>72* | --- |
| 7-CAC-PAC | 12.7 | 4.81 | >>72* | --- |
| DAP | 4.2 | 4.78 | >>72* | --- |
| PAC | 5.5 | 4.78 | >>72* | --- |

RT = HPLC retention time in minutes using the protocol described in the text.

Figure 5 - Table 2

Selected NMR proton chemical shifts in deuterated chloroform and HPLC retention times for paclitaxel and various derivatives.

| compound | NH | CH3' | CH2' | CH13 | CH10 | CH7 | RT |
|---|---|---|---|---|---|---|---|
| paclitaxel | 6.95 | 5.79 | 4.78 | 6.24 | 6.28 | 4.40 | 21 |
| 7-CAC-PAC | 7.05 | 5.80 | 4.81 | 6.19 | 6.14 | 5.62 | 34 |
| 2',7-bis-CAC-PAC | 6.95 | 6.02 | 5.59 | 6.23 | 6.18 | 5.65 | 39 |
| 10-deacetylpaclitaxel | 7.08 | 5.78 | 4.78 | 6.19 | 5.18 | 4.21 | 16 |
| 7-CAC-DAP | 7.05 | 5.79 | 4.78 | 6.19 | 5.27 | 5.52 | 24 |
| 2',7-bis-CAC-DAP | 6.95 | 6.00 | 5.59 | 6.25 | 5.31 | 5.58 | 33 |
| 2',7,10-tri-CAC-DAP | 6.85 | 6.02 | 5.58 | 6.25 | 6.25 | 5.63 | 35 |
| 7-MAC-PAC | 7.06 | 5.81 | 4.80 | 6.19 | 6.12 | 4.63 | 19* |

Chemical shift values are reported in ppm relative to TMS;
RT = HPLC retention time in minutes using the protocol described in the Experimental Section for the analytical HPLC assays deploying either a Discovery or a Suplecosil (*) column.

METHOD FOR THE SELECTIVE REMOVAL OF ACYL-FUNCTIONALITY ATTACHED TO THE 2'-HYDROXY-GROUP OF PACLITAXEL-RELATED DERIVATIVES

This application claims the benefit of Provisional application Ser. No. 60/327,406, filed Oct. 5, 2001.

BACKGROUND OF THE INVENTION

The present invention is generally directed to an efficient method to remove acyl-groups appended by an ester linkage to the 2'-hydroxyl group present in paclitaxel-related molecules.

Paclitaxel (PAC) is an important anticancer drug. However, because of its low water solubility, the formulations needed to deliver PAC by intravenous injection are less than ideal. Thus, considerable attention has been directed toward improving the aqueous solubility of PAC, particularly by pursuing prodrug strategies that take advantage of the C7 or C2' hydroxyl groups for such incorporations. Protecting groups that have been used most frequently during these manipulations include silyl,[1,2] monochloroacetyl[3] (CAC), and trichloroacetyl.[4] Because of its greater reactivity, several investigators have also been able to modify the C2' hydroxyl group directly, i.e. without protecting the C7 hydroxyl functionality.[5-10]

Selective manipulation of the hydroxyl groups present in paclitaxel (PAC) and in 10-deacetylpaclitaxel (DAP) to produce stable analogs and water-soluble prodrugs, has received considerable attention over the course of the last twenty years of PAC-related research.[1-11] Deutsch et al.[3] have shown that among all of the hydroxyl groups present in this family of compounds, the C2' OH is the most reactive toward acylation. When PAC is treated with carbonyldiimidazole, the resulting C2' acylated intermediate can additionally form an oxazolone derivative, an interesting side-reaction more recently encountered by de Groot et al.[4] as well. Amino acid derivatives connected via ester linkages at the C2' position are considerably less stable than when connected at C7 such that the C2' arrangement has been extensively pursued during prodrug strategies. Likewise, Mathew et al.[5] has exploited the instability of C2' esters to produce C7-amino acid esters of PAC by partial, selective hydrolysis of the 2',7-bis-substituted PAC analogs at pH 7.4. Harada et al.[6] have speculated that the instability of the C2' amino acid esters is due to steric repulsion of the bulky groups attached to C2' and C3' as well as to an electronic effect from these types of esters' amino groups. The latter has also been previously implicated by zhao et al.[7] and more recently by Pendri et al.[8] who suggested more specifically that protonation of the amino group could serve to assist attack of the C2' acyl functionality by external nucleophiles due to a simple inductive effect. Other investigators have further postulated that C2' esters of PAC are particularly susceptible to cleavage by various hydrolytic enzymes present in vivo.

SUMMARY OF THE INVENTION

The present invention is directed to the selective removal of acyl-functionalities attached to the 2'-hydroxyl-group of paclitaxel-related derivatives by a convenient and inexpensive solvolytic process that involves dissolving such compounds in an alcohol such as methanol under non-acidic conditions. The temperature and time required to complete the alcoholyses depend upon the nature of the acyl-function and the concentration utilized during the removal reaction. For example, non-sterically hindered acyl-functionalities are readily removed by simply allowing dilute methanolic solutions to stand at ambient temperature for 48 hours.

Because paclitaxel is an expensive starting material, the chemical manipulations for this research program were conducted on a very small scale, namely 50 mg reactions or less. This, in turn, has allowed the inventors to follow reactions and to purify and characterize intermediates by using HPLC. The inventors discovered that the integrity of certain of the HPLC samples appeared to undergo decomposition when the samples were prepared in methanol and examined overnight via an HPLC auto-sampling/injection mode. Upon further studying the decomposition process, it was further discovered that it applied specifically to esters which had been formed by acylating the 2'-hydroxyl-group. The latter represent a common chemical protection maneuver that is deployed on paclitaxel in order to chemically manipulate other portions of the overall molecule, after which the 2'-position protecting group must then be cleaved in a separate step. Previous methods used to cleave such 2'-position protecting groups have involved more complicated reagent systems that do not take the reaction to completion or have involved harsher treatments that are not as selective for the 2'-position relative to other portions of the paclitaxel molecule.

Several paclitaxel analogues have now been prepared whereby the 2'-position protecting group has either been removed in a one-pot fashion after conducting other chemistries, or has been removed in a subsequent, distinct step wherein both approaches have utilized the simple alcoholysis reaction uncovered above.

In addition to the method's use during synthetic medicinal chemistry research, its simplicity, efficiency and environmentally friendly nature as a chemical conversion makes it ideally suited for use in a production chemicals scale mode. It should be appreciated that paclitaxel, while considered to be a wonder-drug in the fight against cancer, is still only a "first-generation" therapeutic agent. Indeed, numerous reports from paclitaxel's use in the clinic speak toward the desire to have improved aqueous solubility, sustained action in multidrug resistant cancers and, like most anticancer chemotherapeutic agents, an enhanced ratio of effects in cancer versus normal cells. Research toward "second-generation" paclitaxel-like compounds has, in turn, led to compounds wherein their synthetic production often traverses the exact same chemical protection, further manipulation and subsequent deprotection strategies for which the present method has the distinct advantages as disclosed herein.

Other objects and advantages of the present invention will become apparent to those skilled in the art upon a review of the following detailed description of the preferred embodiments and the accompanying drawings.

BRIEF DESCRIPTION OF THE DRAWINGS

FIG. 2 is a Table 1 showing the stability of PAC and DAP CAC analogs in methanol (1 mg/ml) at ambient temperature.

TR=Retention Time on reverse phase HPLC; NMR=Nuclear Magnetic Resonance peak for the C2'H; $T_{1/2}$=Half-life Product=Breakdown Product (loss of 2'-acyl group).

Figure 3:
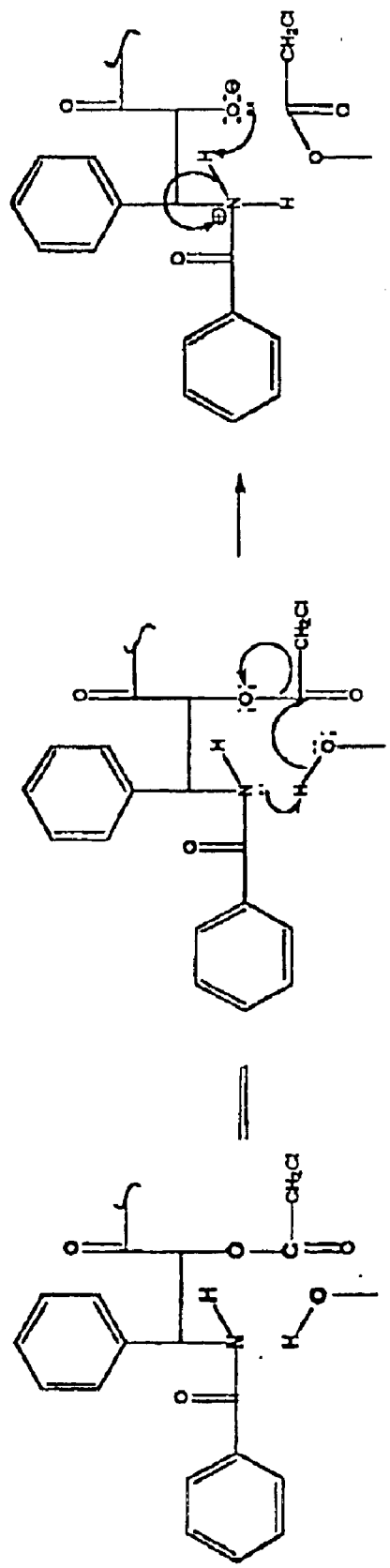

FIG. 3 is a diagram showing a mechanistic model for the methanolysis of PAC-related 2'-esters wherein the neighboring 3'-amide nitrogen atom catalyzes the reaction by serving as a nucleophilic hydrogen bond/proton acceptor.

Figure 4:
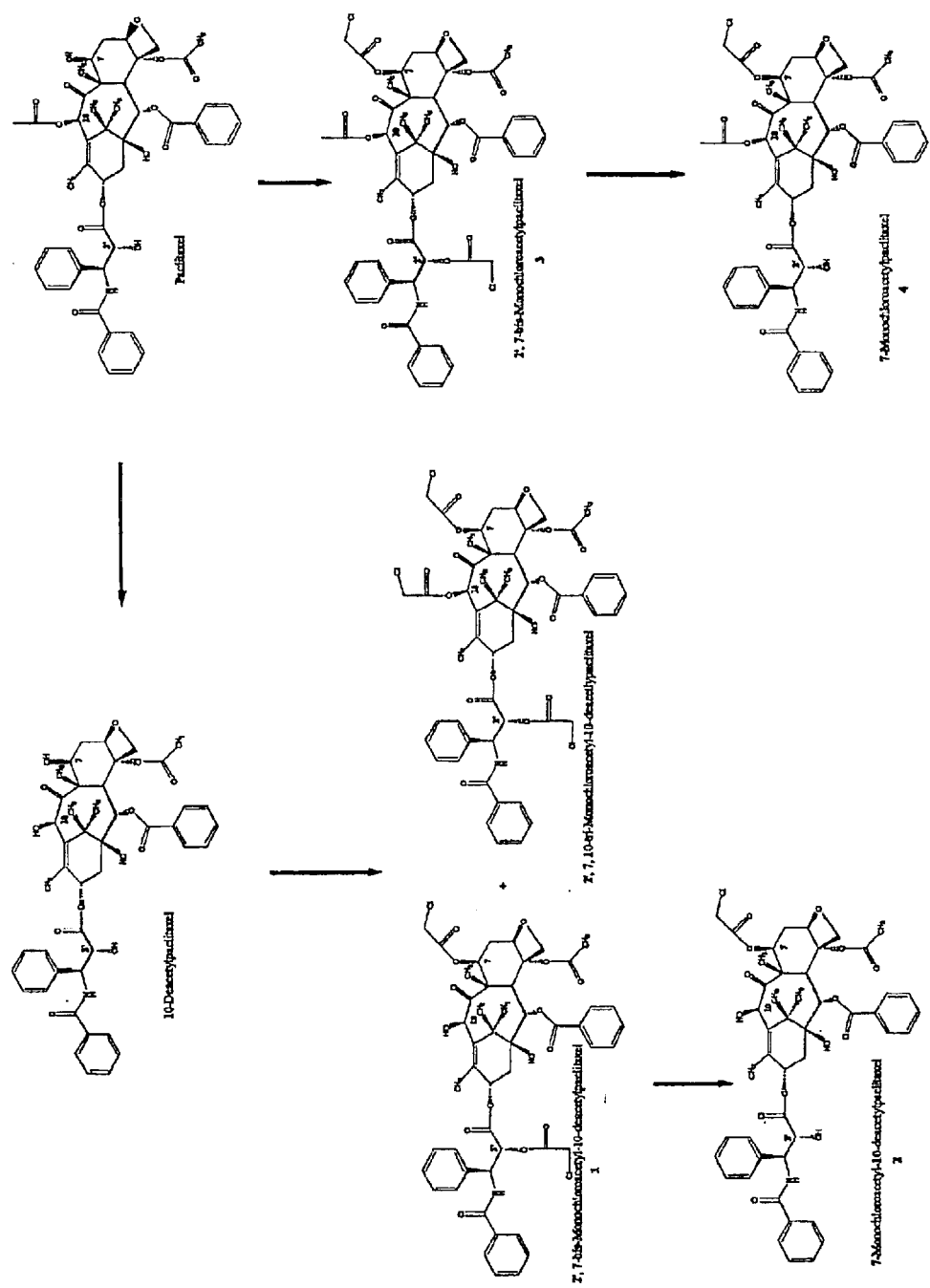

FIG. 4 is a schematic diagram showing reaction schemes leading to compounds 1 to 4. In both sequences, the last chemical conversion to produce either 2 or 4 was readily accomplished by using the methanolysis reaction described herein. Compound 5 was prepared analogously to 4 except that methoxyacetyl was used instead of chloroacetyl.

FIG. 5 is a Table 2 showing selected NMR proton chemical shifts in deuterated chloroform and HPLC retention times (RT) for paclitaxel and various derivatives.

DETAILED DESCRIPTION OF THE PREFERRED EMBODIMENT

During development of an HPLC method to purify 2',7-bis-monochloroacetyl-10-deacetylpaclitaxel (2',7-bis-CAC-DAP), the inventors discovered that the compound was unstable in methanol solution at a concentration of 1 mg/ml. After confirming this observation and characterizing the breakdown product as 7-CAC-DAP the inventors further discovered that such treatments might represent a convenient, general method to selectively remove ester functionalities from the 2'-position during synthetic manipulations of the PAC framework.[14] Interestingly, we also found that more concentrated methanolic solutions, namely 20 mg/ml for use in preparative HPLC, did not appear to undergo solvolysis. Likewise, the use of methanol to quench unreacted acylating reagent immediately after chloroacetylation did not appear to disturb the C2' ester, the latter reflecting a derivatized DAP concentration of 4 mg/ml in total solvent having an acidic pH. Thus, we decided to further investigate the apparent differences in the stability of several PAC and DAP CAC esters relative to concentration and acidity. The compounds we examined are shown in FIG. 2-Table 1.

Figure 1:
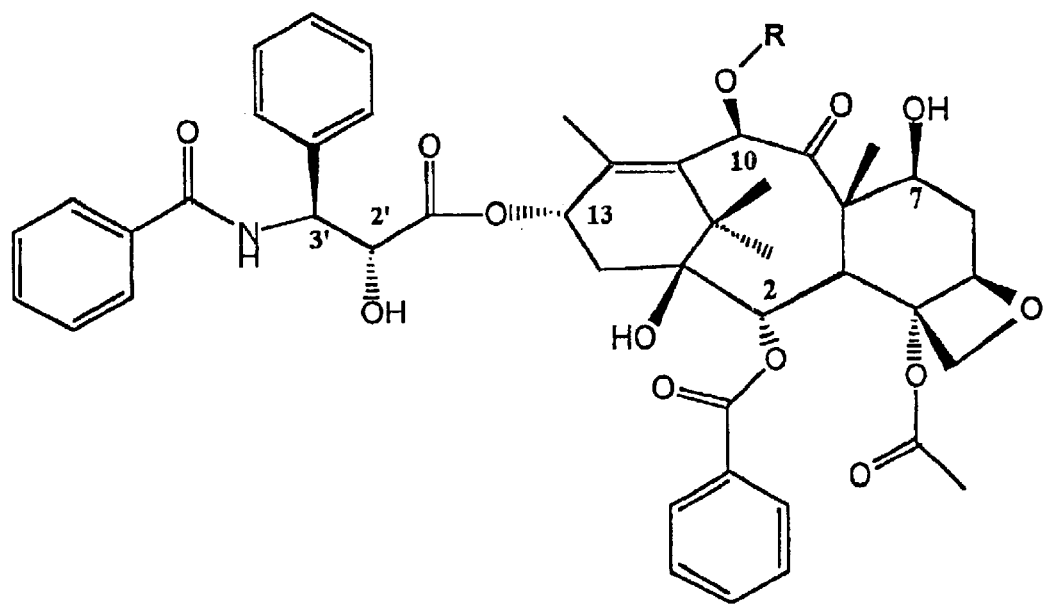
FIG. 1 is a diagram showing structures of paclitaxel (PAC), 10-deacetylpaclitaxel (DAP) and selected derivatives. For PAC, R=COCH$_3$; For DAP, R=H; For the monocloroacetyl (CAC) derivatives, a ClCH$_2$CO— adduct replaces one or more of the hydroxy group hydrogens located at positions C2', C7 and C10. For the methoxyacetyl (MAC) derivatives, a CH$_3$OCH$_2$CO— adduct replaces one or more of the hydroxy group hydrogens located at positions C2', C7 and C10.

Compound abbreviations are provided in FIG. 2-Table 1 according to the nomenclature and numbering specified in FIG. 1. RT=Retention times on an analytical HPLC (Waters) equipped with a reversed-phase column (Supleco Discovery C18) using a gradient elution (60% acetonitrile from 0–2 min., linearly ramped from 60% to 75% from 2–12 min., and held steady at 75% for the duration of the assay) at a flow rate of 1.2 ml/min. monitored by UV detection (225 nm). NMR (CDCl$_3$) values for the C2' proton shifts are in ppm relative to TMS. $T_{1/2}$=Apparent half-lives. All compounds were independently prepared and characterized by HPLC, NMR and elemental analyses. †Previously reported by Rao et al. ††Previously reported by Rimoldi et al.[21] *Less than 5% breakdown after 72 hr.

A 1 mg/ml solution of 2',7-bis-CAC-DAP in methanol was allowed to stand at ambient temperature. 20 µl samples were withdrawn at T=0, 2, 24 and 48 hrs. Longer incubations were deployed for compounds showing little breakdown. Aliquots were assayed directly by HPLC after establishing that responses obtained for serial dilutions of a freshly prepared 10 mg/ml stock solution of 2',7-bis-CAC-DAP were linear throughout the concentration range anticipated for the samples. A decay curve was generated by following the decrease in compound peak area versus time. An apparent half-life ($T_{1/2}$) was then calculated from a semi-log plot using Microsoft Excel. The decay curve for 2',7-bis-CAC-DAP appears to follow pseudo first-order kinetics typical for solvolysis reactions. The $T_{1/2}$ value for conversion to 7-CAC-DAP is 5.5 hrs. The product growth curve matches very closely with the compound decay curve. Similar results were obtained for all of the other 2'-chloroacetylated derivatives listed in FIG. 2-Table 1 except for 2' CAC-DAP whose $T_{1/2}$ appears to be about three-times longer (18 hrs.). Nevertheless, this derivative is still much more labile than the chloroacetyl esters placed at either the 7- or 10-positions ($T_{1/2}$ values all >>72 hrs.). For example, when 7-CAC-DAP was studied for up to 120 hrs., no significant breakdown to DAP was detected.

For the more concentrated experiments, a 10 mg/ml solution of 2',7-bis-CAC-DAP was allowed to stand at ambient temperature. 10 µl aliquots were withdrawn and diluted with 90 µl of acetonitrile such that 20 µl samples could subjected to the HPLC analysis at the same concentrations used in the previous assays. As before, isolation and crystallization of the product followed by complete characterization confirmed its structure as 7-CAC-DAP. It can be noted that the NMR chemical shifts for the C2' proton among the various family members are diagnostic for loss of the 2'-CAC esters (FIG. 2-Table 1 and FIG. 5-Table 2). For the more concentrated case, however, the apparent $T_{1/2}$ was found to be 16.2 hrs. suggesting that increased sample concentration can have a protective effect upon solvolysis. Likewise, when the 1 mg/ml studies were repeated in the presence of 0.2% acetic acid, the decay curves again suggested that there is a protective effect on hydrolysis. For the weakly acidic studies, less than 4% breakdown of 2',7-bis-CAC-DAP was observed over 48 hrs. and the calculated $T_{1/2}$ was determined to be >1,000 hrs. Thus, the presence of monochloroacetic acid after acetylation fortuitously serves to protect the product when methanol is used to quench this reaction.

When identical functionalities attached to different locations on the same molecular framework display significantly different chemical reactivity, the involvement of neighboring groups as either catalysts or inhibitors of such reactions is likely to be operative.[15] An especially important case for catalysis occurs when the participating groups can adopt orientations analogous to a favorable ring system while the reaction traverses its transition state. In 2',7-bis-paclitaxel-related esters, the 2'-ester functionality resides in close proximity to the 3'-amide group. The latter can provide nucleophilic catalysis via either its carbonyl oxygen or its nitrogen lone pair.[16] Normally, the electron density of the nitrogen lone pair is partially displaced by its resonance relationship with the carbonyl such that the overall system is planar and the oxygen typically serves as the predominant nucleophile. However, in this case the adjacent phenyl ring also donates electrons to the carbonyl such that there is a relative increase in the localization of the lone pair on nitrogen, an increase in the nitrogen's tetrahedral character, and an increase in its capacity to serve as a nucleophile.[16] That this type of catalysis would be expected to be very sensitive to acidification compared to having the oxygen play such a role, is in line with the experimental observation that the overall solvolysis is dramatically attenuated in weakly acidic solutions.

As shown in FIG. 3, the 2'-ester, the 3'-amide nitrogen, and one molecule of methanol can be placed in an arrangement wherein the six atoms that participate in the reaction (bolded) become oriented in a spatial relationship that resembles a six-membered ring. In this model, the amide nitrogen serves as a nucleophilic hydrogen bond acceptor to effect neighboring group catalysis of the methanolysis reaction by enhancing the nucleophilicity of the methanol oxygen. While a concerted mechanism is also possible, the resulting transesterification has been depicted as a two-step process in order to emphasize the catalytic role initially played by the nitrogen lone pair.

The concept of neighboring nucleophile-assisted hydrolysis of 2'-PAC esters was used by Nicolaou et al.[11] in their design of PAC prodrugs. For example, the rate of PAC release was found to increase across the series $HOOCCH_2XCH_2COO$-2'-PAC according to the electron-withdrawing nature of the heteroatom systems placed at X. In this case, however, the proposed mechanism initially involves complete removal of the carboxylic acid proton under basic conditions such that the resulting anion can then effect nucleophilic attack of the ester carbonyl located, by design, to be six atoms away.

The mechanism depicted in FIG. 3 would be expected to be accompanied by pseudo first order kinetics wherein the apparent half-life should be independent of substrate concentration. While this is exactly what appears to be happening in dilute solutions, we also observed that more concentrated solutions have extended half-lives. One possible explanation for this seeming paradox is that the PAC-related materials may be forming aggregates as their concentrations are increased. In this regard, PAC has been observed by others to form concentration-dependent aggregates in non-polar media such as chloroform[17] and to undergo hydrophobic-driven, conformational collapse of the C13 side chain in polar media.[18] While the latter would presumably occur in a concentration independent manner, another way for the lipophilic C13 side chains to avoid protic, polar solvents would be to cluster among two or more PAC molecules, a process that would be promoted by increasing concentration. Clustering of the C13 side chains, in turn, would be expected to limit the access of methanol to the 3'-amide-catalyzed, 2'-ester-reaction area. The implications of our findings on the pharmacological profiles and structure-activity relationships for the PAC-related family of compounds are also important relative to recent models for PAC's association with microtubules.[19,20] For example, Snyder et al.[20] has recently reported a binding conformation in which β-tubulin's His-229 imidazole ring appears to become flanked by the phenyl rings from PAC's 3'-benzamido and 2-benzoyl moieties. The chemical model shown herein suggests that such a stacked arrangement could be further stabilized by hydrogen bonding or even proton transfer between the nucleophilic benzamide nitrogen and an imidazole N—H depending upon the latter's state of protonation.

As part of research to better understand the interaction of PAC-related compounds with various components within cancer cells,[11,12] the inventors deployed CAC protection of both PAC and 10-deacetylpaclitaxel (DAP) (FIG. 4). During purification of various mixtures of the three predominate CAC derivatives obtained for DAP, namely the 2'-mono-, the 2',7-bis- and the 2',7,10-tri-CAC protected materials, the 2'-adducts appeared to be unstable when allowed to stand for prolonged periods in methanol. Testing purified materials on a 1 mg scale confirmed this observation. Moving to a larger sample, a 40 mL solution of 2',7-bis-CAC-DAP was then examined at a concentration of 1 mg/mL. Methanolysis of the 2'-adduct was complete after 48 hours at ambient temperature. The exclusive product was isolated by evaporation of solvent, washed with cold water, and its structure characterized as 7-mono-CAC-DAP according to NMR (FIG. 5-Table 2) and elemental analysis. A similar study starting with 2',7-bis-CAC-PAC behaved exactly the same to provide 7-mono-CAC-PAC. In this case the structural integrity for the latter was additionally confirmed by its independent synthesis analogous to a literature procedure[4] wherein after treatment of PAC with chloroacetic anhydride in pyridine, the reaction mixture was subjected to 10 mM ammonia at room temperature for 1 hour prior to preparative HPLC separation of the resulting mixture of esters.

The chloroacetylation reactions and subsequent alcoholysis can be run in a one-pot manner as long as care is taken to insure that the reaction media is no longer acidic during the second step, e.g. neutralization by addition of a tertiary amine or via a single wash with dilute sodium bicarbonate. The combination of these steps otherwise appears to be quite general and thus the overall method provides a gentle means of selectively manipulating functionality onto the C7-hydroxyl group within PAC and DAP-related systems. Thus, the method is particularly amenable toward the production of sensitive PAC and DAP-related derivatives that intend to bear modified substituents in the C7 and/or C10 positions. Furthermore, reactions that are sluggish, including those involving more concentrated levels of substrate, can be conveniently expedited by warming the solutions at any temperature up to the boiling point of the alcohol. Likewise, aqueous alcoholic solutions, as well as anhydrous solutions, can also be conveniently deployed as a solvent system having any percentage of water up to levels that do not interfere with the inherent solubility of the substrate.

Experimental Section

General Methods

Organic solvents and reagents were used as received from Fisher Scientific Co. and from Aldrich Chemical Co., respectively. Paclitaxel was received as a gift from Yew Tree Pharmaceuticals, Ltd. Deacetylpaclitaxel was obtained by hydrolysis of paclitaxel according to a literature method [13] after modification to eliminate the use of hydrogen peroxide in the presence of tetrahydrofuran. Aqueous solutions were prepared from their respective inorganic reagents as received from J. T. Baker, Inc. Dry nitrogen gas was used as received from AGA Gas Co. Reactions were stirred magnetically and cooling was achieved by using dry ice/acetone baths. Organic phases were dried over anhydrous magnesium sulfate or potassium carbonate (J. T. Baker reagent grade) and brought to 2 to 3° C. prior to filtering. Evaporation of solvents was accomplished on a Buchi rotary evaporator connected to a water aspirator for reduced pressure. Drying of materials within desicators was done at ambient temperature and pressure/low vacuum pressure, employing Drierite/Indicating Drierite and sodium hydroxide purchased from Fisher Scientific. TLC was conducted by using Whatman silica bound to polyester-backed fluorescent indicator (F254) plates purchased from Fisher Scientific. Preparative HPLC was conducted on a Waters Delta Prep 3000 system equipped with a Waters C18 Deltapak column. Samples were loaded via 32% acetonitrile/water using a flow rate of 10 mL/min. and a 100 mL wash. A gradient elution (32% going to 50% acetonitrile over a 50 min. time period) was then applied at a flow rate of 20 mL/min. Effluent was monitored at 225 nm and fractionated between peaks. Fractions corresponding to pure materials were pooled and their products extracted with dichloromethane after evaporation of the acetonitrile. Analytical HPLC was performed on a Waters system equipped with either a Supleco Discovery C18 column or a Suplecosil C18 column using a gradient elution of 40% acetonitrile in water going to 85% over a 45 min. time period or 50% acetonitrile in water going to 95% over a 45 min. time period, respectively, with both having a flow rate of 1 mL/min. monitored at 225 nm. Melting points were determined on an Electrothermal digital melting point apparatus and are uncorrected. Proton NMR spectra were recorded at 30° C. on a Varian 400-MHz Fourier transform spectrometer in CDCl$_3$ (Cambridge Isotope Laboratories, Inc.) using TMS as the internal standard (δ 0.00). IR spectra were recorded at ambient temperature on a Perkin Elmer model 1600 FT-IR Spectrophotometer using 3M type 62 IR cards purchased from Aldrich Chemical Co. Elemental analyses were performed by Atlantic Microlab Inc.

EXAMPLE 1

Non-Aqueous, Ambient Temperature Conditions

2',7-bis-Monochloroacetyl-10-deacetylpaclitaxel (2',7-bis-CAC-DAP) (1). [3] 10-Deacetylpaclitaxel (DAP) (81 mg, 0.10 mmol) and dimethylaminopyridine (DMAP) (5 mg) were dissolved in 1 mL of dimethylformamide (DMF) and a solution of monochloroacetic anhydride (43 mg, 0.25 mmol) in 5 mL dichloromethane (DCM) was added. The mixture was stirred at room temp. for 20 min. and 25 mL of DCM and 1 mL of water were added. The DCM solution was washed with 10 mL water, 10 mL sat. sodium bicarbonate, 10 mL water, and then dried over sodium sulfate. The DCM was evaporated and the residue dried over NaOH to provide 85 mg. of crude product. Analytical HPLC indicated two peaks having an area ratio of 2 to 1. The dried residue was dissolved in 1 mL of acetonitrile and loaded on a C18 Deltapack preparative column and eluted according to the general method. The effluent was fractionated and fractions corresponding to pure products were pooled. Yield: 43 mg (0.45 mmol, 45%) of 1 having 93% purity by HLPC; mp 160–163° C. (lit. [3] 166–168° C.); Analytical HPLC RT=33 min. (Discovery column); Elemental Analysis calculated for formula $C_{49}H_{51}Cl_2NO_{15} \cdot 2H_2O$: C, 58.80%; H, 5.54%; N, 1.40%. Found: C, 58.52%; H, 5.62%; N, 1.32%. Also isolated 8 mg (0.08 mmol) of 2',7,10-tri-CAC-DAP having 98% purity by HPLC; mp 157° C. softens (lit. [3] 154–155° C.); Analytical HPLC RT=35 min. (Discovery column); Elemental Analysis Calculated for formula $C_{51}H_{52}Cl_3NO_{16} \cdot H_2O$: C, 57.82%; H, 5.14%; N, 1.32%. Found: C, 57.52%; H, 5.11%; N, 1.28%. Characteristic proton NMR chemical shifts for both products are provided in FIG. 5-Table 2.

7-Monochloroacetyl-10-deactylpaclitaxel (7-CAC-DAP) (2). 2',7-bis-CAC-DAP (1) (30 mg, 0.031 mmol) was dissolved in 40 mL of methanol (HPLC grade) and left at ambient temperature. 20 μL samples were withdrawn at several hour intervals and analyzed directly by HPLC. The conversion was complete in 48 hrs. Solvent was evaporated to dryness leaving a glossy residue which crystallized upon addition of water. Yield: 25 mg (0.028 mmol) having 97% purity by HPLC; mp 163–166° C.; Analytical HPLC RT=24 min. (Discovery column); Elemental Analysis calculated for formula $C_{47}H_{50}ClNO_{14}$: C, 63.55%; H, 5.67%; N, 1.58%. Found: C, 63.08%; H, 5.97%; N, 1.63%. Characteristic proton NMR chemical shifts are provided in FIG. 5-Table 2.

2',7-bis-Monochloroacetylpaclitaxel (2',7-bis-CAC-PAC) (3). Paclitaxel (43 mg, 0.05 mmol), DMAP (10 mg) and chloroacetic anhydride (40 mg, 23 mmol) were dissolved in 0.2 mL of DMF and 4 mL DCM. The mixture was allowed to react at room temperature. 20 μL samples were withdrawn at several minute intervals and analyzed by HPLC. After about 1 hour the reaction was complete. The reaction mixture was diluted with 25 mL DCM and the resulting solution washed with brine. Solvent was evaporated and the residue crystallized from methanol (2 mL) and brine (3 mL). Yield: 46 mg (0.046 mmol, 92%) having 97% purity by HPLC; mp 209–211° C. (lit. [3] mp not reported); Analytical HPLC RT=39 min. (Discovery column). Characteristic proton NMR chemical shifts are provided in FIG. 5-Table 2.

7-Monochloroacetylpaclitaxel (7-CAC-PAC) (4). 1 mg of 2',7-bis-CAC-PAC (3) was dissolved in 1 mL of methanol and the solution left at ambient temperature. 20 μL samples were withdrawn at several hour intervals and directly analyzed by HPLC. The conversion was complete in 48 hours. The product was identical (Table 1 HPLC and NMR data) with 7-CAC-PAC obtained by chloroacetylation of PAC in pyridine, followed by hydrolysis using ammonia and purification by preparative HPLC.[4] Alternatively, 7-CAC-PAC can be obtained via a one-pot protocol starting from PAC. Hence, after acetylation of PAC according to the method for 3, the reaction mixture was diluted with DCM and washed with sodium bicarbonate and brine. The solution was then dried over $Na_2SO_4$ and the solvents were removed. The 47 mg residue was dissolved in 50 mL methanol and left at room temperature for 48 hours after which solvent was removed and the residue crystallized upon addition of water. It should be noted that it is important to remove all traces of chloroacetic acid when using the one-pot process. Overall yield: 39 mg (0.48 mmol, 97%) having 99% purity by HPLC; mp 152–156° C. (darkening); Analytical HPLC RT=34 min. (Discovery column); Elemental Analysis calculated for formula $C_{49}H_{52}Cl NO_{15}$: C, 63.26%; H, 5.63%; N, 1.51%. Found: C, 62.80%; H, 5.93%; N, 1.41%. Characteristic proton NMR chemical shifts are provided in FIG. 5-Table 2.

EXAMPLE 2

Non-Aqueous, Elevated Temperature Conditions

7-Methoxyacetylpaclitaxel (7-MAC-PAC) (5). 2',7-bis-MAC-PAC (30 mg, 0.03 mmol), prepared analogously to 1 and 3, was dissolved in 60 ml of methanol and the solution stirred at 47° C. Samples (20 μl) were withdrawn at several hour intervals and analyzed directly by HPLC. Nearly 90% conversion occurred within 7 hours. Solvent was evaporated and the residue purified by preparative HPLC. Overall yield: 22 mg (0.024 mmol, 80%) having 99% purity by HPLC; mp 132–136° C.; Analytical HPLC RT=19 min. (Suplecosil column); Elemental analysis calculated for $C_{50} H_{55} NO_{16} \cdot H_2O$: C, 63.36%; H, 6.09%; N, 1.48%. Found: C, 63.95%; H, 6.35%; N, 1.35%. Characteristic proton NMR chemical shifts are provided in FIG. 5-Table 2

EXAMPLE 3

Aqueous Ethanol, Ambient Temperature Conditions

7-Monochloroacetyl-10-deacetylpaclitaxel (7-CAC-DAP) (2). 2',7-bis-CAC-DAP (0.71 mg, 0.0007 mmol) was dissolved in 0.71 ml of 80% ethanol/20% water and left at ambient temp. 20 μl samples were withdrawn at several hour intervals and analyzed directly by HPLC. Approximately 20% conversion occurred in 22 hours as quantitated by analytical HPLC (substrate RT=21 min. and product RT=16 min. using the Suplecosil column and elution protocol). The product was identified by HPLC comparison with an analytical sample of 7-CAC-DAP (Example 1).

EXAMPLE 4

Aqueous Ethanol, Elevated Temperature Conditions

7-Monochloroacetyl-10-deacetylpaclitaxel (7-CAC-DAP) (2). 2',7-bis-CAC-DAP (0.70 mg, 0.0007 mmol), was, dissolved in 0.7 ml of 80% ethanol/20% water and the solution stirred at 56° C. 20 µl samples were withdrawn at several hour intervals and analyzed directly by HPLC. Approximately 50% conversion occurred in 24 hours as quantitated by analytical HPLC (substrate RT=21 min. and product RT=16 min. using the Suplecosil column and elution protocol). The product was identified by HPLC comparison with an analytical sample of 7-CAC-DAP (Example 1).

The above detailed descriptions of the present invention are given for explanatory purposes. It will be apparent to those skilled in the art that numerous changes and modifications can be made without departing from the scope of this invention. In particular, it is apparent that the range of paclitaxel-related derivatives spans all types of compounds beyond the immediate analogues of paclitaxel or docetaxel with the only requirement being that an analogous 3'-nitrogen-containing system is present and remains unobstructed so that it can assist in the reaction according to the disclosed mechanism. Likewise, it is apparent that the range of acyl-functionality that can be removed from the 2'-oxygen atom spans all types of compounds beyond the simple protecting groups conveyed herein with the only requirement being that the immediate environment of the acyl-moiety remains unencumbered by significant steric bulk such as would occur when the position alpha to the carbonyl is tri-substituted with large groups. The latter substitution pattern is also an obvious limitation for the types of alcohols that can be deployed during the reaction to attack the acyl-functionality. Accordingly, the whole of the foregoing description is to be construed in an illustrative and not a limitative sense, the scope of the invention being defined solely by the appended claims wherein the use of the phrases "acyl-groups" and "paclitaxel-related molecules," along with the term "alcohol," in all cases are meant to convey the widest possible array of these compounds within the limits of their aforementioned constraints.

The following references are disclosed herein and are fully incorporated herein by reference.

1. Rao, K. V.; Bhakuni, R. S.; Johnson, J.; Oruganti, R. S. *J. Med. Chem.* 1995, 38, 3411.
2. Georg, G. I.; Chen, T. T.; Ojima, I.; Vyas, D. M. Editors. *Taxane Anticancer Agents*; Am. Chem. Soc.: Washington, D.C., 1995.
3. Deutsch, H. M.; Glinski, J. A.; Hernandez, M.; Haugwitz, R. D.; Narayanan, V. L.; Suffness, M.; Zalkow, L. H. *J. Med. Chem.* 1989, 32, 788.
4. de Groot, F. M. H.; van Berkom, L. W. A.; Scheeren, H. W. *J. Med. Chem.* 2000, 43, 3093.
5. Mathew, A. E.; Mejillano, M. R.; Nath, J. P.; Himes, R. H.; Stella, V. J. *J. Med. Chem.* 1992, 35, 145.
6. Harada, N.; Ozaki, K; Yamaguchi, T.; Arakawa, H.; Ando, A; Oda, K; Nakanishi, N.; Ohashi, M.; Hasiyama, T.; Tsujihara, K *Heterocycles* 1997, 46, 241.
7. Zhao, Z.; Kingston, D. G. I.; Crosswell, A. R. *J. Nat. Prod.* 1991, 54, 1607.
8. Pendri, A.; Canover, C. D.; Greenwald, R. B. *Anti-Cancer Drug Design* 1998, 13, 387.
9. Dubowchik, G. M.; Mosure, K.; Knipe, J. O.; Firestone, R. A *Bioorg. Med. Chem. Letters* 1998, 8, 3347.
10. Safavy, A.; Raisch, K. P.; Khazaeli, M. B.; Buchsbaum, D. J.; Booner, J. A. *J. Med. Chem.* 1999, 42, 4919.
11. Nicolaou, K. C.; Riemer, C.; Kerr, M. A.; Rideout, D.; Wrasidlo, W. *Nature* 1993, 364, 464.
12. Erhardt, P. *The Taxane Journal*, 1997, 3, 36.
13. Sarver, J.; Klis, W.; Byers, J.; Erhardt, P. *J. Biomolec. Screening* Submitted.
14. Klis, W. A.; Sarver, J. G.; Erhardt, P. W. *Synth. Comm.* Submitted.
15. March, G. *Advanced Organic Chemistry: Reactions, Mechanisms and Structure*; Wiley: New York, 1985.
16. Kirby, A. J.; Fersht, A. R. Progress Bioorg. Chem. 1971, 1, 1.
17. Balasubramanian, S. V.; Straubinger, R. M. *Biochem.* 1994, 33, 8941.
18. Vander Velde, D. G.; Georg, G. I.; Grunewald, G. L.; Gunn, C. W.; Mitscher, L. A *J. Am. Chem. Soc.* 1993, 113, 11650.
19. Li, Y.; Poliks, B.; Cegelski, L.; Poliks, M.; Gryzynski, Z.; Piszczek, G.; Jagtap, P. G.; Studelska, D. R.; Kingston, D. G. I.; Schaefer, J.; Bane, S. *Biochem.* 2000, 39, 281.
20. Snyder, J. P.; Nettles, J. H.; Cornett, B.; Downing, K. H.; Nogales, E. *Proc. Nat Acad. Sci. USA* 2001, 98, 5312.
21. Rimoldi, J. M.; Kingston, D. G. I.; Chaudhary, A. G.; Samaranayake, G.; Grover, S.; Hamel, E. *J. Nat. Products* 1993, 56, 1313.
22. Green T. W.: Wuts, P. G. M. Protective Groups in Organic Synthesis, Third Edition. Wiley: New York, 1999.
23. Zheng, Q. Y.; Darbie, L. G. G\Cheng, X.; Murrary, C. K. *Tet. Lett.* 1995, 36, 2001.

We claim:

1. A method for removing acyl-groups appended by an ester linkage to the 2'-hydroxyl group present in paclitaxel-related molecules comprising treatment with alcohol under non-acidic conditions.

2. The method of claim 1 wherein the treatment is conducted at ambient temperature.

3. The method of claim 1 wherein the treatment is conducted at elevated temperature.

4. The method of claim 2 wherein the alcohol also contains water.

5. The method of claim 3 wherein the alcohol also contains water.

6. A method for removing acyl-groups appended by an ester linkage to the 2'-hydroxyl group present in paclitaxel-related molecules comprising treatment with a methanolic or ethanolic solution under non-acidic conditions.

7. The method of claim 6 wherein the treatment is conducted at ambient temperature.

8. The method of claim 6 wherein the treatment is conducted at elevated temperatures.

9. The method of claim 7 wherein the alcohol also contains water.

10. The method claim 8 wherein the alcohol also contains water.

11. A method for converting 2',7-bis-monochloroacetylpaclitaxel, 2',7-bis-monochloracetyl-10-deacetylpaclitaxel or 2',7-bis-monochloroacetyldocetaxel to their corresponding 7-monochloroacetyl derivatives by treatment with an anhydrous or aqueous alcohol system under non-acidic conditions.

12. The method of claim 11 wherein the alcohol is either methanol or ethanol and the treatment is conducted at ambient temperature.

13. A method for converting 2',7-bis-methoxyacetylpaclitaxel, 2',7-bis-methoxyacetyl-10-deacetylpaclitaxel or 2',7-bis-methoxyacetyldocetaxel to their corresponding 7-methoxyacetyl derivatives by treatment with an anhydrous or aqueous alcohol system under non-acidic conditions.

14. The method of claim 13 wherein the alcohol is either methanol or ethanol and the treatment is conducted at elevated temperature.

* * * * *